(12) United States Patent
Preissman

(10) Patent No.: US 6,348,055 B1
(45) Date of Patent: Feb. 19, 2002

(54) NON-COMPLIANT SYSTEM FOR DELIVERY OF IMPLANT MATERIAL

(75) Inventor: Howard Preissman, San Jose, CA (US)

(73) Assignee: Parallax Medical, Inc., Scotts Valley, CA (US)

( * ) Notice: Subject to any disclaimer, the term of this patent is extended or adjusted under 35 U.S.C. 154(b) by 0 days.

(21) Appl. No.: 09/688,721

(22) Filed: Oct. 16, 2000

Related U.S. Application Data (62) Division of application No. 09/276,062, filed on Mar. 24, 1999, now abandoned.

(51) Int. Cl.[7] .................................................. A61F 5/04
(52) U.S. Cl. ........................................ 606/94; 604/264
(58) Field of Search .............................. 606/92, 93, 94; 604/207, 208, 211, 218, 224, 264

(56) References Cited

U.S. PATENT DOCUMENTS

| | | | |
|---|---|---|---|
| 29,083 A | | 7/1860 | Irving |
| 3,701,771 A | | 10/1972 | Almen et al. |
| 3,750,667 A | | 8/1973 | Pshenichny et al. |
| 3,835,860 A | | 9/1974 | Garretson |
| 3,882,858 A | | 5/1975 | Klemm |
| 3,919,773 A | | 11/1975 | Freeman |
| 4,189,065 A | | 2/1980 | Herold |
| 4,274,163 A | * | 6/1981 | Malcom et al. |
| 4,288,355 A | | 9/1981 | Anderson et al. |
| 4,312,343 A | | 1/1982 | LeVeen et al. |
| 4,338,925 A | * | 7/1982 | Miller |
| 4,341,691 A | | 7/1982 | Anuta |
| 4,364,921 A | | 12/1982 | Speck et al. |
| 4,373,217 A | | 2/1983 | Draenert |
| 4,404,327 A | | 9/1983 | Crugnola et al. |
| 4,469,109 A | | 9/1984 | Mehl |
| 4,554,686 A | | 11/1985 | Baker |
| 4,576,152 A | * | 3/1986 | Muller et al. |
| 4,585,035 A | | 4/1986 | Piccoli |
| 4,595,006 A | | 6/1986 | Burke et al. |
| 4,610,692 A | | 9/1986 | Eitenmuller et al. |
| 4,637,931 A | | 1/1987 | Schmitz |
| 4,653,487 A | * | 3/1987 | Maale |
| 4,653,489 A | * | 3/1987 | Tronzo |
| 4,670,008 A | | 6/1987 | Von Albertini |
| 4,671,263 A | | 6/1987 | Draenert |
| 4,699,178 A | | 10/1987 | Washkewicz et al. |
| 4,728,570 A | | 3/1988 | Ashman et al. |
| 4,776,704 A | | 10/1988 | Kopunek et al. |
| 4,791,150 A | | 12/1988 | Braden et al. |
| 4,793,363 A | | 12/1988 | Ausherman et al. |
| 4,795,444 A | | 1/1989 | Hasegawa et al. |
| 4,798,596 A | | 1/1989 | Mühlbauer |
| 4,813,871 A | | 3/1989 | Friedman |
| 4,815,454 A | * | 3/1989 | Dozier, Jr. |

(List continued on next page.)

FOREIGN PATENT DOCUMENTS

| | | | |
|---|---|---|---|
| DE | 3443167 A1 | * | 6/1986 |
| DE | 42 19 563 A1 | | 12/1993 |
| EP | 0261182 B1 | | 3/1988 |
| WO | WO 92/04924 A1 | | 4/1992 |
| WO | WO 97/04657 A1 | | 2/1997 |

OTHER PUBLICATIONS

Cotten et al. (1996). "Preoperative Percutaneous Injection if Methyl Methacrylate and N–Butyl Cyanoacrylate in Vertebral Hemangiomas," *AJNR* 17:137–142.

(List continued on next page.)

*Primary Examiner*—David O. Reip
(74) *Attorney, Agent, or Firm*—Bozicevic, Field & Francis LLP; Frank P. Becking (57) ABSTRACT

A substantially non-compliant conduit for delivery an implant material from a high pressure applicator to an implant delivery device. Also, a high pressure, substantially non-compliant system for delivery of accurate volumes of implant material to the desired site.

12 Claims, 7 Drawing Sheets

U.S. PATENT DOCUMENTS

| | | | |
|---|---|---|---|
| 4,837,279 A | | 6/1989 | Arroyo |
| 4,838,282 A | | 6/1989 | Strasser et al. |
| 4,900,546 A | | 2/1990 | Posey-Dowty et al. |
| 4,921,479 A | | 5/1990 | Grayzel |
| 4,929,238 A | | 5/1990 | Baum |
| 4,966,601 A | | 10/1990 | Draenert |
| 4,969,888 A | | 11/1990 | Scholten et al. |
| 4,986,814 A | | 1/1991 | Burney et al. |
| 5,014,717 A | | 5/1991 | Lohrmann |
| 5,015,101 A | | 5/1991 | Draenert |
| 5,108,404 A | * | 4/1992 | Scholten et al. ............... 606/94 |
| 5,112,354 A | | 5/1992 | Sires |
| 5,195,526 A | | 3/1993 | Michelson |
| 5,282,861 A | | 2/1994 | Kaplan |
| 5,304,586 A | | 4/1994 | Hammesfahr et al. |
| 5,336,263 A | | 8/1994 | Ersek et al. |
| 5,336,699 A | | 8/1994 | Cooke et al. |
| 5,341,816 A | | 8/1994 | Allen |
| 5,346,495 A | | 9/1994 | Vargas, III |
| 5,361,806 A | | 11/1994 | Lalikos et al. |
| 5,367,002 A | | 11/1994 | Huang et al. |
| 5,372,583 A | | 12/1994 | Roberts et al. |
| 5,398,483 A | | 3/1995 | Smith et al. |
| 5,451,406 A | | 9/1995 | Lawin et al. |
| 5,456,267 A | | 10/1995 | Stark |
| 5,476,880 A | | 12/1995 | Cooke et al. |
| 5,507,813 A | | 4/1996 | Dowd et al. |
| 5,527,298 A | | 6/1996 | Vance et al. |
| 5,571,182 A | | 11/1996 | Ersek et al. |
| 5,574,075 A | | 11/1996 | Draenert |
| 5,591,171 A | | 1/1997 | Brown |
| 5,653,730 A | | 8/1997 | Hammerslag |
| 5,658,332 A | | 8/1997 | Ducheyne et al. |
| 5,660,186 A | | 8/1997 | Bachir |
| 5,660,210 A | | 8/1997 | Ikeda et al. |
| 5,676,146 A | | 10/1997 | Scarborough |
| 5,681,317 A | | 10/1997 | Caldarise |
| 5,681,872 A | | 10/1997 | Erbe |
| 5,702,446 A | | 12/1997 | Schenck et al. |
| 5,788,702 A | | 8/1998 | Draenert |
| 5,792,478 A | | 8/1998 | Lawin et al. |
| 5,795,922 A | | 8/1998 | Demian et al. |
| 5,928,468 A | * | 7/1999 | Tolson ........................ 156/578 |
| 5,951,160 A | | 9/1999 | Ronk |
| 6,016,845 A | | 1/2000 | Quigley et al. |
| 6,039,084 A | | 3/2000 | Martucci et al. |
| 6,080,801 A | | 6/2000 | Draenert et al. |
| 6,086,569 A | | 7/2000 | Schweizer |

OTHER PUBLICATIONS

Cybulski. (Aug. 1989). "Methods of Surgical Stabilization for Metastatic Disease of the Spine," *Neurosurgery* 25(2):240–252.

Deramond. (Aug. 1989). "Percutaneous Vertebroplasty With Methyl–Methacrylate; Technique, Method, Results," *Neurosurgery* 25(2):Space 269.

Harrington. (1986). "Anterior Decompression and Stabilization of the Spine as a Treatment for Vertebral Collapse and Spinal Cord Compression From Metastatic Malignancy," *Clin. Orthopaedics and Related Research* pp. 177–197.

Sundaresen et al. (1985). "Treatment of Neoplastic Epidural Cord Compression by Vertebral Body Resection and Stabilization," *J. Neurosurg.* 63:676–684.

Weill et al. (1996). "Spinal Metastases; Indications for and Results of Percutaneus Injection of Acrylic Surgical Cement," *Radiology* 199:241–247.

Convery, R. et al. (1975). "The relative safety of polymethylmethacrylate," *J. of Bone and Joint Surg.* 57–A(1):57–64.

Dierks, E. J. et al. (1992). "Treatment of an infected mandibular graft using tobramycin–impregnated methylmethacrylate beads: Report of a case," *J. Oral Maxillofac. Surg.* 50:1243–1245.

Galibert, P. et al. (1987). "Note préliminaire sur le traitement des angiomes vertébraux par vertébroplastie acrylique percutané," *Neurochirurgie* 33:166–168. (Partial summary translation included.).

Goode, R. L. and Reynolds, B. N.. (Feb. 1992). "Tobramycin–impregnated methylmethacrylate for mandible reconstruction," *Arch Otolaryngol. Head Neck Surg.* 118:204.

Kammerlen, P. et al. (1989). "Vertébroplastic percutanée dans le traitement des métastases: Technique et résultats," *J. Radiol.* 70(10):557–562. (Partial summary translation included.).

McLaughlin, R. E. et al. (1973). "Blood clearance and acute pulmonary toxicity of methylmethacrylate in dogs after simulated arthroplasty and intravenous injection," *J. of Bone and Joint Surg.* 55–A(8):1621–1628.

Nicola, N. and Lins, E. (1987). "Vertebral hemangioma: Retrograde embolization ——Stabilization with methyl methacrylate," *Surg, Neuro.l* 27:481–486.

O'Donnell, R. J. et al. (Dec. 1994). "Recurrence of giantcell tumors of the long bones after currettage and packing with cement," *J. of Bone and Joint Surg* 76–A(12):1827–1833.

Persson, B. J. et al. (1984). "Favourable results of acrylic cementation for giant cell tumors," *Acta Orthop. Scand.* 5:209–214.

Phillips, H. et al. (Aug. 21, 1971). "Cardiovascular effects of implanted acrylic bone cement," *British Medical Journal* 3:460–461.

Shapiro, S. A.. (1991). "Cranioplasty, vertebral body replacement, and spinal fusion with tobramycin–impregnated methylmethacrylate," *Neurosurgery* 28(6):789–791.

Stringham, D. R. et al. (1994). "Percutaneous transpedicular biopsy of the spine," *Spine* 19(17):1985–1991.

Wang, G. et al. (Feb. 1984). "Safety of anterior cement fixation in the cervical spine: In vivo study of dog spine," *So. Med. J.* 77(2):178–179.

* cited by examiner

NON-COMPLIANT SYSTEM FOR DELIVERY OF IMPLANT MATERIAL

This application is a divisional of application Ser. No. 09/276,062 filed on Mar. 24, 1999 now abandoned.

TECHNICAL FIELD

The present invention relates to systems for more accurately controlling the placement of implant materials percutaneously or otherwise under pressurized flow. Procedures for such placement include procedures for the repair of hard tissue by injection of hard tissue implant materials, such as in hip augmentation, mandible augmentation, and particularly vertebroplasty, among others. Procedures also include the placement of implant materials in soft tissues.

BACKGROUND ART

Polymethylmethacrylate (PMMA) has been used in anterior and posterior stabilization of the spine for metastatic disease, as described by Sundaresan et al., "Treatment of neoplastic epidural cord compression by vertebral body resection and stabilization." *J Neurosurg* 1985;63:676–684; Harrington, "Anterior decompression and stabilization of the spine as a treatment for vertebral collapse and spinal cord compression from metastatic malignancy." *Clinical Orthodpaedics and Related Research* 1988;233:177–197; and Cybulski, "Methods of surgical stabilization for metastatic disease of the spine." *Neurosurgery* 1989;25:240–252.

Deramond et al., "Percutaneous vertebroplasty with methyl-methacrylate: technique, method, results [abstract]." *Radiology* 1990;117 (suppl):352; among others, have described the percutaneous injection of PMMA into vertebral compression fractures by the transpedicular or paravertebral approach under CT and/or fluoroscopic guidance. Percutaneous vertebroplasty is desirable from the standpoint that it is minimally invasive, compared to the alternative of surgically exposing the hard tissue site to be supplemented with PMMA or other filler.

A general procedure for performing percutaneous vertebroplasty involves placing a cannula with an internal stylet into the desired implantation site. The cannula and stylet are used in conjunction to pierce the cutaneous layers of a patient above the hard tissue to be supplemented, then to penetrate the hard cortical bone of the vertebra, and finally to traverse into the softer cancellous bone underlying the cortical bone. Once positioned in the cancellous bone, the stylet is then removed leaving the cannula in the appropriate position for delivery of a hard tissue implant material to reinforce and solidify the damaged hard tissue.

A syringe is next loaded with polymethyl methacrylate (PMMA) and connected to the end of the cannula that is external of the patient's body. Pressure is applied to the plunger of the syringe to deliver the PMMA to the site of damaged bone at the distal end of the cannula. Because in general, 10 cc syringes are only capable of generating pressures of about 100–150 psi, this places a limitation on the viscosity of the PMMA that can be effectively "pushed through" the syringe and cannula and fully delivered to the implant site. Of course, the use of a small barrel syringe, e.g., a 1 cc syringe enables the user to generate higher driving pressures. For example pressures of 800 psi and possibly as high as 1000–1200 psi (depending upon the strength of the user and the technique) may be generated using a 1 cc syringe. A serious limitation with the use of a 1 cc syringe, however, is that it will not hold a large enough volume to complete the procedure in one step or "load" and must be reloaded several times to complete the procedure, since, on average, about 3.5 cc of implant material per side of the vertebral body are required for an implantation procedure. This makes the procedure more complicated with more steps, and more risky in that the polymerization of the implant material causes it to become increasingly more viscous during the additional time required for reloading. Another problem with a 1 cc syringe is lack of control, as high pressures are generated in a "spike-like" response time and are not continuously controllable.

A viscous or syrupy consistency of PMMA is generally believed to be most advantageous for performing percutaneous vertebroplasty. Such a consistency insures that the implant material stays in place much better than a less viscous, more liquid material. Additionally, when PMMA is implanted percutaneously, the need to inject it through a relatively narrow needle or cannula also greatly increases the need for a high pressure driver. Still further, implantation of PMMA into a relatively closed implantation site (e.g., trabecular bone) further increases the resistance to flow of the PMMA, at the same time increasing the pressure requirements of the driver. Thus, a high pressure applicator that has enough storage capacity to perform a complete implantation procedure without having to reload the device in the midst of the procedure, and which is consistently controllable, for an even, constant application of pressure during delivery of the entirety of the implant material is preferred.

Attempts have been made to increase the ability to apply pressure to drive PMMA to the vertebral implant site by providing a smaller barrel syringe, but this holds less volume and must be refilled once or several times to deliver enough volume of PMMA to the site. Since there is a limited amount of time to work with PMMA before it begins to polymerize or set up, this type of procedure is more difficult to successfully complete within the allotted time, and thus poses an additional risk to the success of the operation. An improved high pressure applicator disclosed in U.S. application Ser. No. 09/053,108, has been developed for controllably applying higher pressures to a source of hard tissue implant material to successfully implant the material at the desired location in a single batch, for the performance of hard tissue implantation and particularly for percutaneous vertebroplasty. U.S. application Ser. No. 09/053,108 is hereby incorporated by reference in its entirety.

Leakage or seepage of PMMA from the vertebral implant site can cause a host of complications some of which can be very serious and even result in death. For example, Weil et al. reported cases of sciatica and difficulty in swallowing which were related to focal cement leakage, *Radiology* 1996;Vol 199, No. 1,241–247. A leak toward the distal veins poses an even more serious risk, since this can cause a pulmonary embolism which is often fatal. In addition to misplacement of the cannula away from the intended implant site, leakage or seepage also may occur even when the cannula is properly placed. For example, overfilling of the intended implant site, under pressure, can result in seepage or leakage after removal of the cannula from the implant site.

Overfilling can occur simply by injecting a larger volume of implant material than the void to be filled at the implant site. Additionally, due to the high pressures involved in the implant procedure, compliance within the delivery system can act as a capacitance under pressure, thereby storing a volume of the implant material and energy under pressure. Upon release of the pressure at the pressure applicator end, the compliant portion of the system also releases its energy and consequently drives an additional amount of implant material into the implant site, thereby overfilling the intended implant site. Upon removal of the delivery system, a leakage or seepage problem ensues at the implant site as a result of the overfilling.

In a known arrangement disclosed by Tronzo in U.S. Pat. No. 4,653,489, a fenestrated hollow hip screw is adapted for delivery of bone cement to an osteoporitic hip fracture site in a femur. The screw is permanently fixed to the femur by screwing it thereto. Once the screw is mechanically fixed to the femur, bone cement is injected into the site by a 20 cc syringe through a standard intravenous (IV) extension tube which connects with a cannulation in the screw. In this situation, the cannulation is large and therefor a relatively lower driving pressure is required for delivery of the bone cement as compared to the situations described above. Additionally, the fact that the screw stays in place even after the injection of the bone cement helps to lessen the occurrence of seepage or leakage.

Nevertheless, compliance of the IV tubing allows the tubing walls to expand upon initial application of pressure by the syringe, thereby decreasing the response performance of the arrangement. That is, the walls of the tubing expand, thereby storing a certain amount of bone cement therein, before the bone cement moves forward and into the implantation site. Additionally, the relative elasticity of the tubing walls stores energy upon expansion thereof Consequently, when an operator first applies a driving force to the plunger of the syringe to establish a driving pressure to drive the bone cement, immediate flow of the cement to the implantation site does not occur. Rather, the walls of the tubing first stretch and act as a reservoir of the bone cement, and flow does not begin until a threshold pressure required to cause flow of the cement is reached and until no further expansion of the tubing walls occurs. This thereby reduces the response performance of the system.

Additionally, after flow has begun and the decision is made by the operator to stop the flow to the implant site, the operator removes all application of pressure to the bone cement by removing any application of force to the plunger. At this time, the stored energy in the expanded walls is released, thereby returning the IV tube to its pre-pressurization configuration and dimension and driving an additional amount of bone cement through the IV tube and into the implantation site. This additional amount of flow is sometimes referred to as "oozing" or "drip".

Malcolm et al. in U.S. Pat. No. 4,274,163 discloses a prosthetic fixation technique in which pressurized bone cement is injected through a prosthesis and into an implantation site. Although a flexible inlet tubing 24 is used to deliver pressurized cement to the prosthesis, compliance of the tubing is not a concern, since Malcom et al. expects leakage or seepage of the bone cement. Exit cannulae 72 and 74 are provided in the prosthesis through which blood and other bodily fluids are forced out of the implantation site by the introduction of the pressurized cement. Upon observation of a flow of bone cement out of the exit cannulae, the operator knows to stop injecting bone cement. Thus, any oozing or drip upon cessation of the driving pressure is easily accommodated by the exit cannulae.

Dozier, Jr. discloses an injector for directly injecting bone cement into a bone cavity in U.S. Pat. No. 4,815,454. The injector used is an injection gun similar to a caulking gun. The nozzle of the cement cartridge held by the injection gun is inserted into a tapered bore of an expander member and compliant plug which is located in the opening to the implant site. In this situation, a relatively large volume of bone cement is placed and the emphasis of the setup is an application of sufficient pressure to drive the cement into the trabeculae in the implant site.

Figure 10:
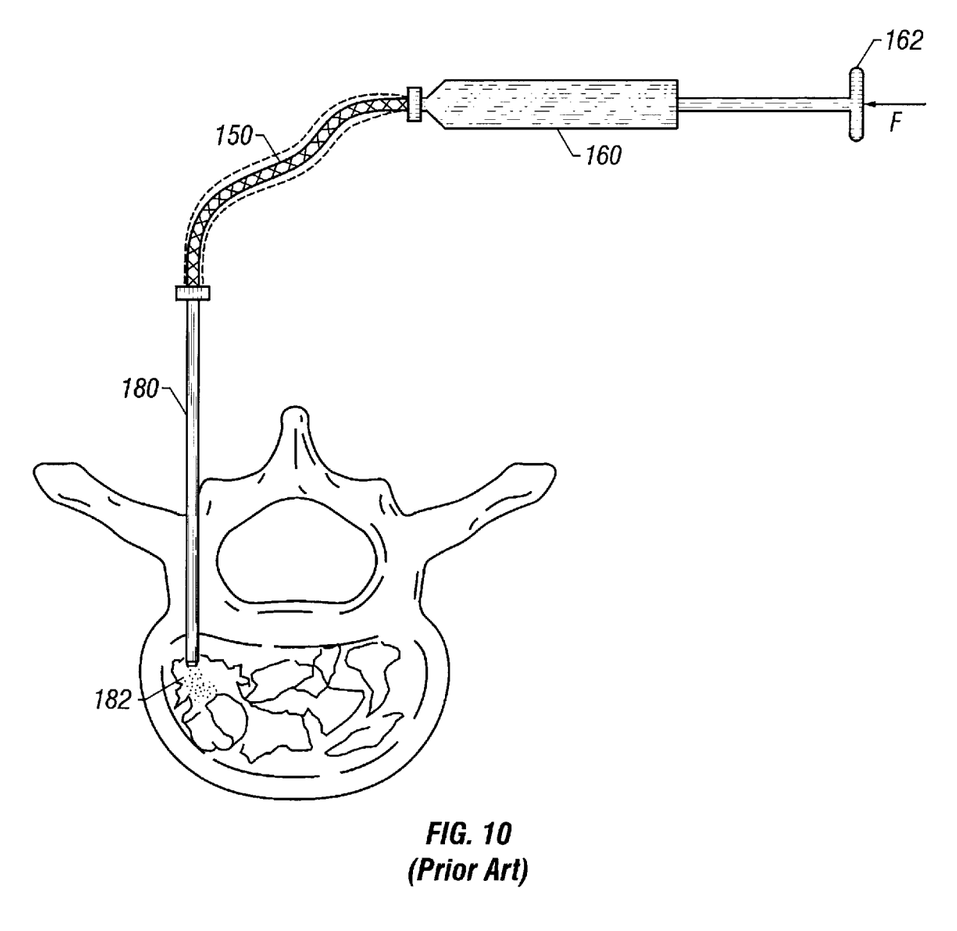
FIG. 10 is a schematic representation of a prior art compliant delivery system, under pressure, being used for percutaneous delivery of a hard tissue implant material.

High pressure extension lines are commercially available, with pressure ratings of up to 1200 psi. These lines are made from materials such as braided polyurethane, braided PVC or PVC tubing. Although capable of withstanding pressures up to about 1200 psi, these lines are compliant and exhibit the same "oozing" or overfilling phenomenon as discussed above, due to the storage of implant material in the expanded volume of the lines under pressure. As shown in FIG. 10, the high pressure extension line 150 radially expands (shown exaggerated in phantom lines) upon application of pressure by the syringe 160 (force F applied to plunger 162), thereby decreasing the response performance of the arrangement. That is, the walls of the tubing 150 expand, thereby acting as a reservoir, storing a certain amount of implant material therein, before the implant material flows forward into the implantation site, and maintains that storage as long as the pressure is maintained.

Consequently, when an operator first applies a driving force F to the plunger 162 of the syringe 160 to establish a driving pressure to drive the implant material, immediate flow of the implant material to the implantation site does not occur. Rather, the walls of the line 150 first stretch and act as a reservoir storing the implant material, and flow does not begin until a threshold pressure required to cause flow of the implant material is reached and until no further expansion of the tubing walls occurs. This thereby reduces the response performance of the system.

Figure 11:
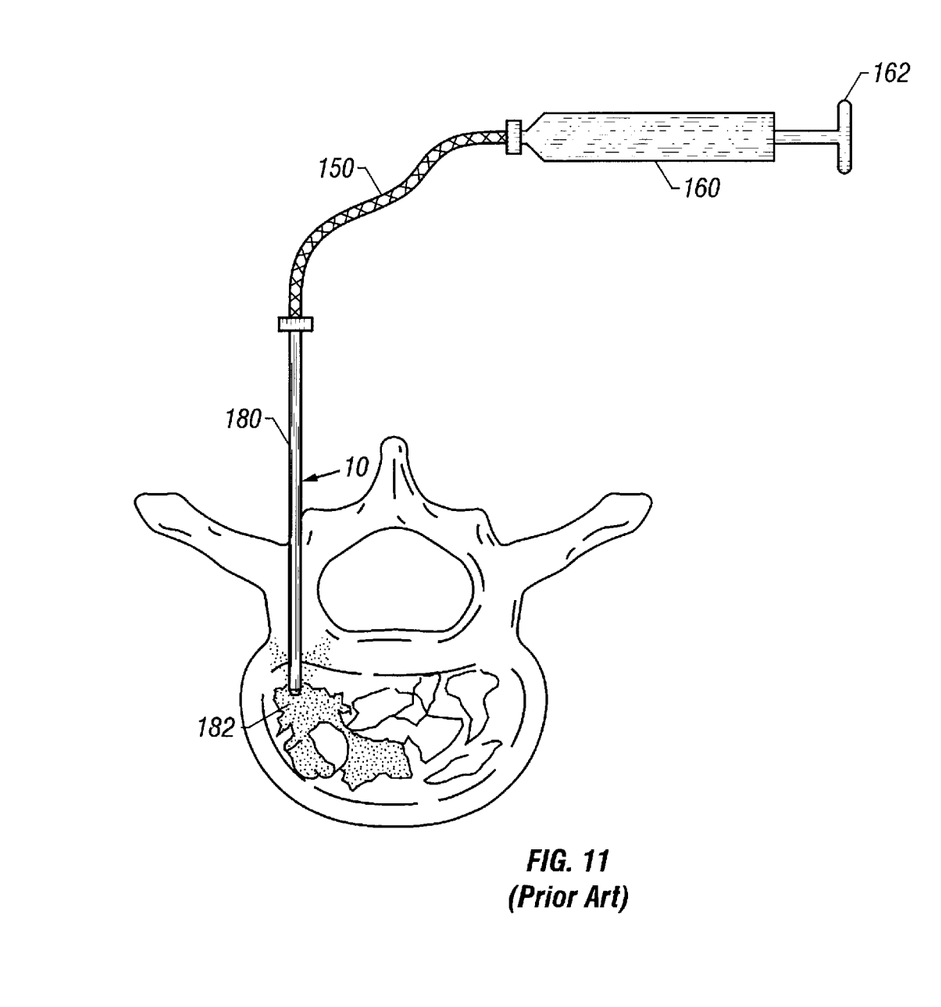
FIG. 11 is a schematic representation of a prior art compliant delivery system, with the pressure removed after percutaneous delivery of implant material to a hard tissue site, illustrating the "oozing" phenomenon.

After flow has begun into the implant site, the operator monitors the filling of the site. When it is observed that the site has been substantially filled, and the decision is made by the operator to stop the flow to the implant site, the operator removes all application of pressure to the implant material by removing any application of force F to the plunger 162. At this time, the stored energy in the expanded walls is released, and the elasticity of the high pressure line 150 returns it to its pre-pressurization configuration and dimension, shown in FIG. 11. Since the system is closed at the end of the line 150 connected to the syringe 160, the contraction of the line 150 drives an additional volume of the implant material to the open end of the system, i.e., the opening 182 at the end of cannula 180, which often leads to overfilling.

Thus, there exists a need for an improved system and procedure for controllably applying higher pressures to a source of implant material to successfully and accurately implant a volume of the material at the desired location in a single batch, while at the same time enables both the applicator, and thus the user's hand to be distanced from the radiographic field or other viewing field. In particular there is a need for an improved system for the performance of percutaneous vertebroplasty.

DISCLOSURE OF THE INVENTION

The present invention includes a substantially non-compliant conduit for delivering implant material under high pressure, from a pressure source to a device which delivers the material to an implant site. The conduit preferably comprises a substantially non-compliant tube having first and second ends, which are adapted to be removably fixed to the pressure source and the device, respectively.

The conduit preferably has a burst pressure at least 2,000 psi , more preferably at least about 2,500 psi and up to at least about 4,000 psi. The conduit may or may not have a reinforcing structure. In the embodiments employing a reinforcing structure, the reinforcing structure is preferably a non-stretch coil within a wall of the conduit. The coil is preferably formed of flat wire, but may also be formed of round wire. Alternatively, the reinforcement may be a braided structure.

Further disclosed is a substantially non-compliant system for percutaneously delivering implant material, which includes a delivery port providing percutaneous access to an implant site; a high pressure applicator for driving the delivery of the implant material; and a substantially non-compliant tube interconnecting said high pressure applicator and said delivery port. A preferred example of a device providing the delivery port is a cannula, but other devices, such as needles may also be employed.

A system for delivering implant material, either percutaneously or otherwise, is disclosed to include a substantially non-compliant delivery device providing access to an implant site; a high pressure applicator for driving the delivery of the implant material; and a substantially non-compliant conduit adapted to interconnect said high pressure applicator and said delivery device.

A method of delivering implant material is also described, in which a substantially non-compliant delivery device is inserted into a tissue site where implantation of an implant material is desired. Next, a substantially non-compliant, high pressure conduit is connected to an input port of the delivery device, and to a high pressure applicator containing a predetermined volume of tissue implant material. After connection of the system a high pressure is applied to the implant material, via the high pressure applicator, to drive the implant material through the conduit and the device and into the site.

BEST MODE FOR CARRYING OUT THE INVENTION

The present invention substantially improves the delivery of implant materials to implant sites, and is especially well suited for percutaneous deliveries. The present invention substantially reduces several of the risk factors associated with the performance of percutaneous bone cement delivery, and particularly addresses the problems of overfilling due to oozing, as described above. Additionally, the present invention enables an increase in an upper acceptable viscosity value of the implant material to be delivered because of the substantial non-compliance of the system according to the present invention, even at high pressures.

An example of a procedure for performing percutaneous vertebroplasty is illustrated in FIGS. 1–6 . A stylet 1 is provided which has a length that is more than sufficient to span the distance from the epidermis of a patient to the cancellous bone tissue in the vertebra, in the preferred configuration. Typically the length of the stylet would be about three inches or greater, but lesser lengths may also be employed as well, depending on the size of the patient. Of course, if other hard tissues are to be accessed, the length of the stylet can be readily modified without departing from the inventive features of the present invention.

The stylet 1 is preferably made of a surgical grade of stainless steel, but other known equivalent biocompatible metals and materials may be used for the same purpose. Ideally, the stylet, or at least a distal end thereof, will be radiopaque so that it can be monitored using fluoroscopy, CT or other imaging techniques during the procedure to help determine the depth and location of the penetration.

Figure 1:
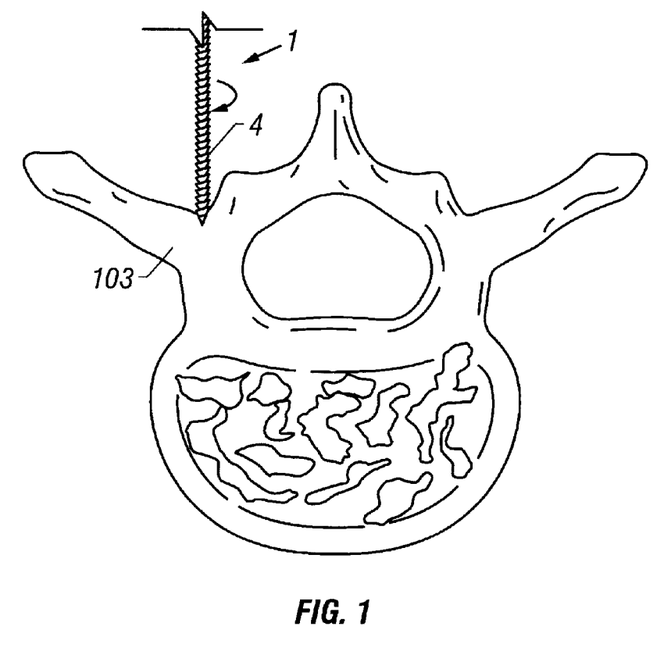
FIG. 1 is a diagram of an initial phase of insertion of a stylet into an implant site.
Figure 2:
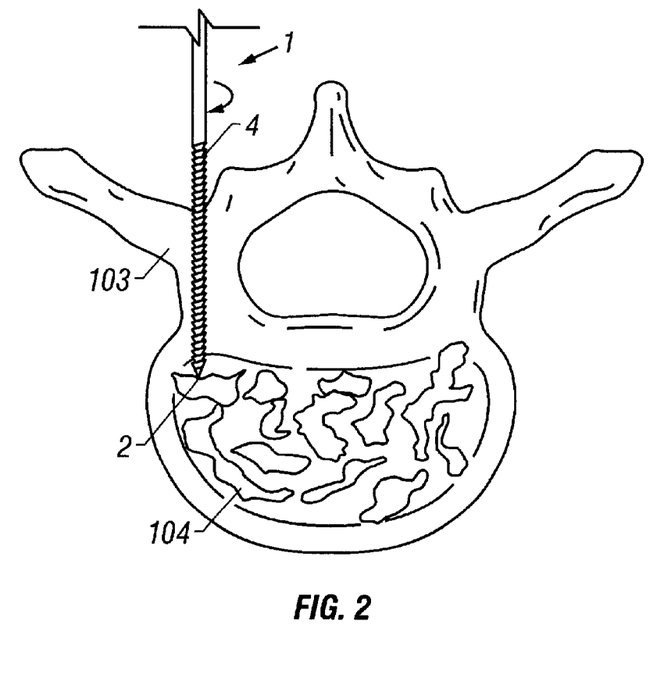
FIG. 2 shows the stylet having penetrated the cortical bone and approaching cancellous bone.

A first or distal end of the stylet 1 ends in a point 2 which is sharp and adapted to penetrate hard tissue when axially loaded. Extending from the tip 2 in the example shown in FIG. 1 are self-tapping threads 4. However, other procedures may employ a stylet which does not have self tapping threads, but rather, is simply forced into the implantation site so that the point 2 pierces a pathway to the site of implantation. The self-tapping threads 4 provide an advantage in that once the tip 2 has penetrated the cortical bone (e.g., see FIG. 2), the operator of the stylet can than proceed to advance the stylet by torquing the stylet, which engages the self-tapping threads 4 in the cortical bone 103 and begins to screw the stylet 1 into the cortical bone 103, as illustrated in FIG. 2.

Turning to FIG. 1, a preferred example of depth guided instruments will now be described. A stylet 1 is provided which has a length that is more than sufficient to span the distance from the epidermis of a patient to the cancellous bone tissue in the vertebra, in the preferred configuration. Typically the length of the stylet would be about three inches or greater, but lesser lengths may also be employed as well, depending on the size of the patient. Of course, if other hard tissues are to be accessed, the length of the stylet can be readily modified without departing from the inventive features of the present invention.

The stylet 1 is preferably made of a surgical grade of stainless steel, but other known equivalent biocompatible metals and materials may be used for the same purpose. Ideally, the stylet, or at least a distal end thereof, will be radiopaque so that it can be monitored using fluoroscopy, CT or other imaging techniques during the procedure to help determine the depth and location of the penetration.

Figure 3:
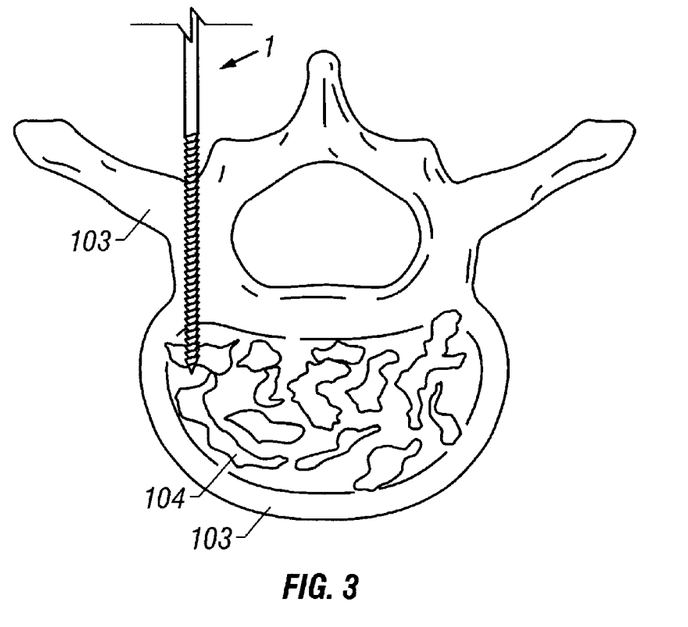
FIG. 3 shows the stylet having reached the desired site of implantation.

A first or distal end of the stylet 1 ends in a point 2 which is sharp and adapted to penetrate hard tissue when axially loaded. Extending from the tip 2 are self-tapping threads 4. The self-tapping threads 4 provide an advantage in that once the tip 2 has penetrated the cortical bone (e.g., see FIG. 2), the operator of the stylet can than proceed to advance the stylet by torquing the stylet, which engages the self-tapping threads 4 in the cortical bone 103 and begins to screw the stylet 1 into the cortical bone 103. Rotation of the stylet 1 is continued, to advance the stylet into the bone, while monitoring the advancement with some type of imaging technique, e.g., fluoroscopy or equivalent. Advancement is continued until the tip 2 reaches the site at which it is desired to deliver the implant material. Usually this site is in the cancellous bone as shown in FIG. 3, but could be anywhere within the bone where there is osteoporosis, fracture or other defect.

A cannula 10 is provided which includes an elongated tubular structure 11 to be positioned in the cancellous bone or other implantation site for delivery of PMMA or other bone implant material therein. The tubular structure 11 of the cannula 10 is preferably made of a surgical grade of stainless steel, but may be made of known equivalent materials which are both biocompatible and substantially non-compliant at operating pressures described herein. Preferably, at least a distal end of the tubular structure is radiopaque. The tubular structure 11 has an inside diameter which is only slightly larger than the outside diameter of the stylet 1, so that the cannula may effortlessly pass axially over the stylet, while at the same time being supported and guided by the stylet. A first or distal end 12 of the cannula is preferably (but not necessarily) beveled to ease the penetration of the cannula through the cutaneous and soft tissues, and especially through the hard tissues.

Surrounding the second end of the tubular structure 11 is a connector 18 (FIG. 6) for linking the cannula 10 with a substantially non-compliant conduit 70 according to the present invention, for supplying the PMMA or other implantable material that is to be injected through the conduit 70 and tubular structure 11. Preferably, connector 18 is a Luer-lock type of connector, but other known connecting mechanisms may be successfully interchanged, e.g., a conventional threaded hole, a threads and locking nut arrangement, etc.

Figure 4:
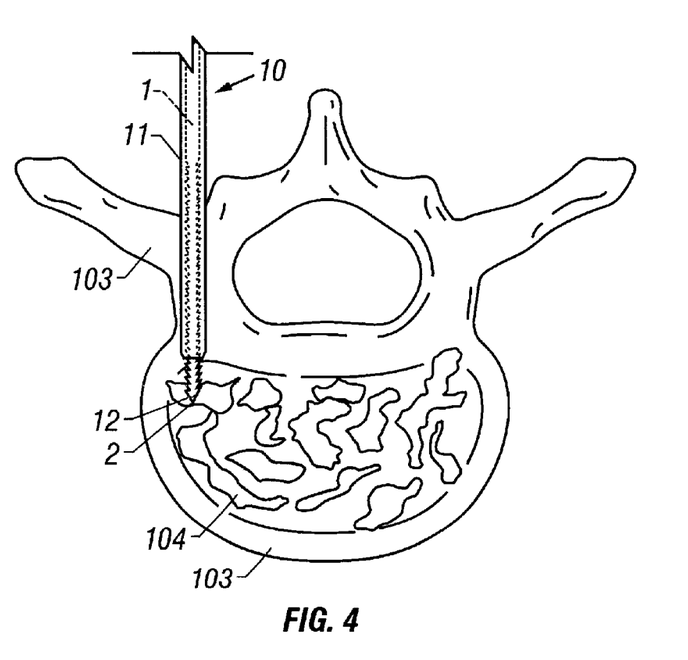
FIG. 4 illustrates the positioning of a cannula by guiding it along the stylet.
Figure 5:
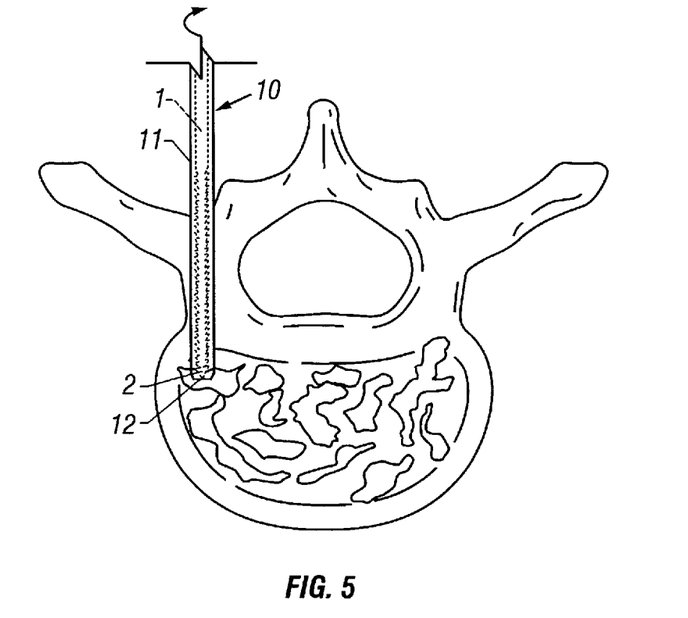
FIG. 5 is a view of the cannula in position at the desired site of implantation, with the stylet still in position.

As shown in FIGS. 4–5, the cannula 10 is advanced over the stylet, until visualization of the process indicates that the end of the cannula 12 is substantially even with the tip of the stylet 2, whereby it is confirmed that the cannula is properly positioned for delivery of the implant material. Next the stylet 1 is removed from the site, either by reverse rotation or by simply withdrawing it. At the same time the cannula 10 is maintained in position to be readied for delivery of the implant material.

Figure 6:
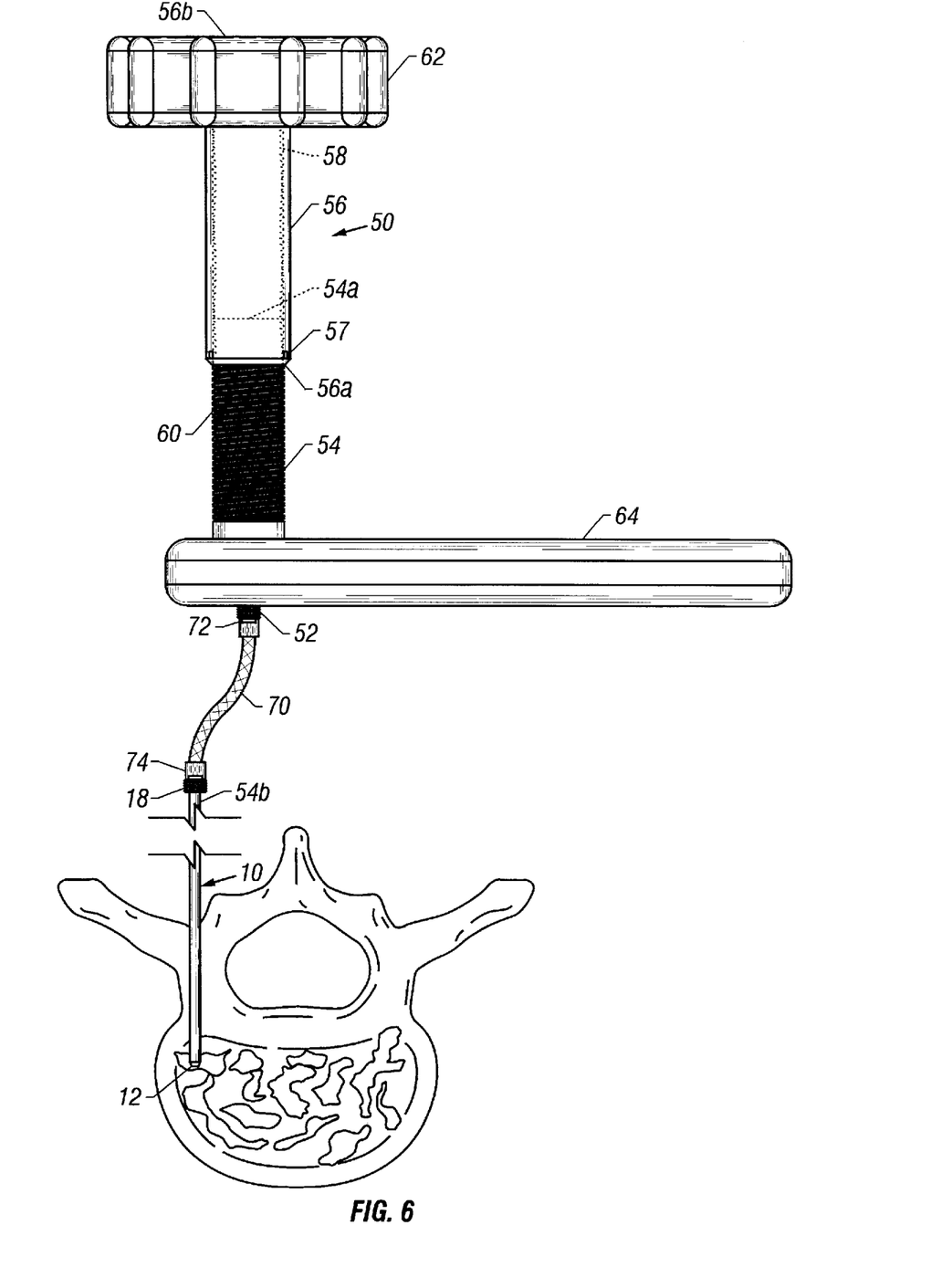
FIG. 6 is a schematic representation of a substantially non-compliant delivery system, according to the present invention, being used for percutaneous delivery of a hard tissue implant material.

A substantially non-compliant pressure applicator 50 is next mounted to the conduit 70, as shown in FIG. 6. The pressure applicator 50 is provided with a fitting 52 which is designed to form a pressure tight connection with the conduit 70. As mentioned above, the preferred type of connection is a Luer-lock type connection, but alternative, equivalent types of connectors may be employed. The pressure applicator further includes a first column 54 for receiving and containing the hard tissue implant material. The first column 54 is open at one end 54a for receiving the implant material. At the other end 54b of the first column is a much smaller opening which ends with the connector or transfer fitting 52.

A second column 56 is provided for overfitting first column 54 and providing a pressure seal therewith. Preferably, the second column is interiorly threaded 58 and the interior threads 58 mate with exterior threads 60 provided on the first column 54. However, other equivalent types of driving arrangements, e.g., a ratchet and pawl arrangement or other equivalent arrangements could be used in place of the mating threads, so long as adequate pressure is able to be generated and maintained between the two columns for providing the driving force for the implant material, and so long as the two columns are substantially non-compliant under such adequate pressure.

Column 56 is open at end 56a for receiving the first column 54 therein. At the opposite end 56b, column 56 is closed to enable a generation of pressure within the two columns as they are moved toward one another and column 56 passes over column 54. Preferably, at least one sealing element 57 (e.g., an O-ring) is provided in the interface between columns 54 and 56 to maintain a high pressure fitting therebetween.

A handle 62 is mounted on the column 56 to provide additional leverage for driving the column 56 with respect to column 54. In the example shown in FIG. 6, the handle 62 is provided at the closed end 56b to provide a greater mechanical advantage for torquing column 56 about its longitudinal axis. Of course, the handle could be provided anywhere along the column 56 so long as it extends the effective radius for torquing about the longitudinal axis. For other types of driving mechanisms other types of handles might be employed. For example, a lever might extend from the column in an embodiment using a ratchet and pawl type of driving mechanism.

A stabilizer 64 is fixedly attached or mounted to the first column 54. The stabilizer 64 may be grasped by the operator and provides leverage against rotation of the first column 54 during driving of the second column 56. Preferably, the stabilizer 64 is in the form of a lever as shown in FIG. 6, but alternative embodiments of the stabilizer may include a circular handle, etc. so long as an equal mechanical advantage is provided to the user.

The above described components of the pressure applicator 50 are all preferably formed of Nylon, polypropylenes, PEEK (polyetheretherketones), PTFE (polytetraflouoroethylenes) or other fluorinated polycarbons. However, any other materials which are durable, sterilizable, biofriendly, chemically compatible with bone cement or whatever implant material is to be delivered, and substantially noncompliant under the operating pressures described herein, such as stainless steel, could be readily substituted.

Figure 7:
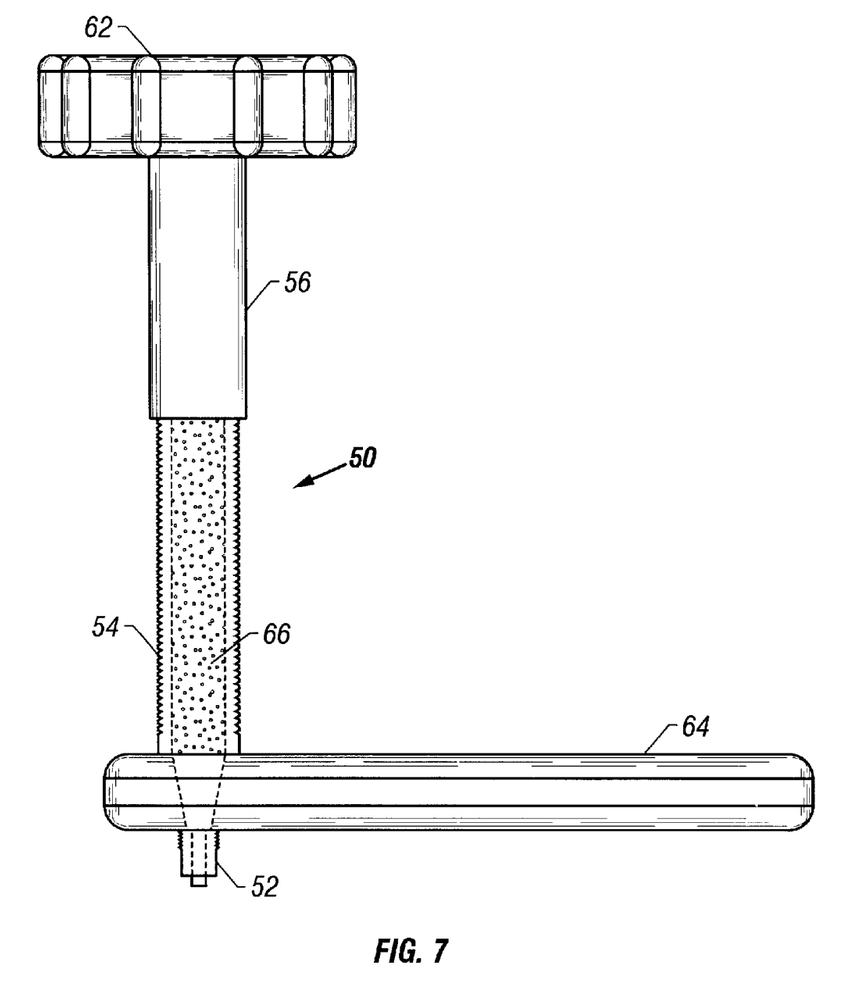
FIG. 7 is a representation of an example of a high pressure applicator filled with implant material prior to interconnecting the system according to the present invention.

Prior to interconnecting the system, a hard tissue implant material 66 is loaded into the first column 54 and the second column 56 is connected with the first column 54 in preparation for implantation, see FIG. 7. Immediately prior, at the same time or immediately subsequent to the loading of the pressure applicator 50, the substantially non-compliant conduit 70 is also preloaded with implant material to avoid an injection of air held by the inner volume of the conduit 70 upon commencement of implantation.

The first column 54 is then rotated slightly with respect to the second column 56 until a minimal amount of tissue implant material is expressed from the fitting 52 end, to ensure that no air has been entrapped in the applicator. The pressure applicator 50 is then secured to the conduit 70 via fittings 52 and 72 to provide a pressure tight seal between the two components. The cannula 10 is backfilled with saline, tissue implant material 66, or other biocompatible fluid in order to displace the air therefrom. The conduit 70 is then mounted onto the cannula 10 as described above and shown in FIG. 6. Alternative methods of connecting the components are described below. The operator next grasps the handle 62 in one hand and the stabilizer 64 in the other and begins to torque the handle 62 while maintaining the stabilizer 64 in its position. When operated as described, the pressure applicator is capable of generating pressures of about 1000 to 2000 psi within the columns, which is a high driving force that is applied to the implantable material 66.

Torquing of the handle 62 with respect to the stabilizer 64 is continued until a sufficient amount of implant material 66 has been delivered to the implant site as verified by an appropriate imaging technique. Advantageously, the pressure applicator 50 allows a first column 54 which is large enough in volume to contain sufficient implant material for an entire implantation process so that there is no need to refill the column 54 in the midst of a procedure. When adequate filling of the implant site has been confirmed by the operator via the imaging apparatus, all torquing of the handle 62 is ceased and the flow of the implant material ceases as well, with substantially no overshoot or oozing.

Figure 8:
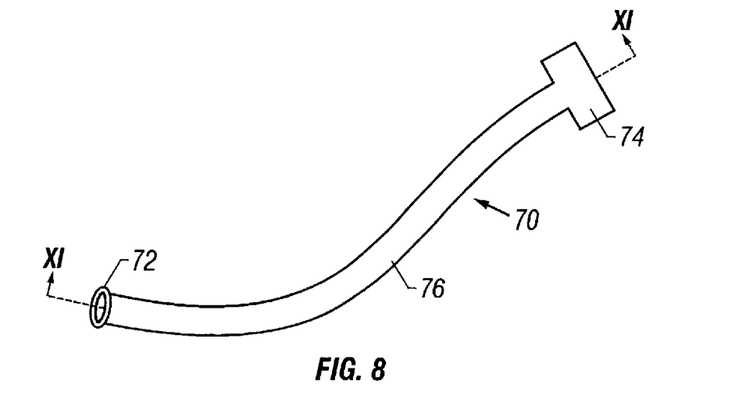
FIG. 8 is a view of an embodiment of a substantially no-compliant tube according to the present invention.

Turning to FIG. 8, one embodiment of a substantially non-compliant, high pressure conduit is exemplified. The meaning of "high pressure" here is defined by structures capable of withstanding pressures of at least 500 psi, and preferably at least 1000 psi, with a burst pressure of at least about 2000 psi. What is meant by "substantially non-compliant" is that a volume change of less than about 25% under pressure, preferably less than 20% and most preferably less than 10% when compared to the same component at atmospheric pressure. In the example of FIG. 8, a flexible tubing 70 is constructed of a polymer which is chemically compatible (e.g., nonreactive) with methylmethacrylate and which is biocompatible. Examples of such polymers are polyvinyl chlorides, Nylon blends, PTFE, FEP and most preferably PEEK. Other equivalent polymers may also be used. Tubing 70 has female 72 and male 74 connectors for forming pressure tight seals with fitting 52 and connector 18, respectively. Of course, either or both of connectors 72 and 74 may be exchanged for its counterpart male/female fitting, while at the same time interchanging the fitting on the corresponding cannula/pressure applicator.

Tubing 70 may be radially reinforced with a non-stretch coil 78 that spirals within the wall of the tubing 70. By "non-stretch" is meant that the coil is substantially non-expandable in the radial directions of the tubing under the described operating pressures. Thus, together as a unit, the tubing wall 76 and reinforcing coil 78, or the tubing wall without a reinforcing coil when the tubing is made of PEEK, for example, exhibit less than 10% change in volume under operating pressures of about 1200 psi, compared to their initial volume under atmospheric pressure. The examples below indicate the compliance performance of several various embodiments of tubing. The burst pressure of tubing 70 is at least in the range of about 2,000 to 2,500 psi, more preferably at least 4000 psi.

Figure 9:
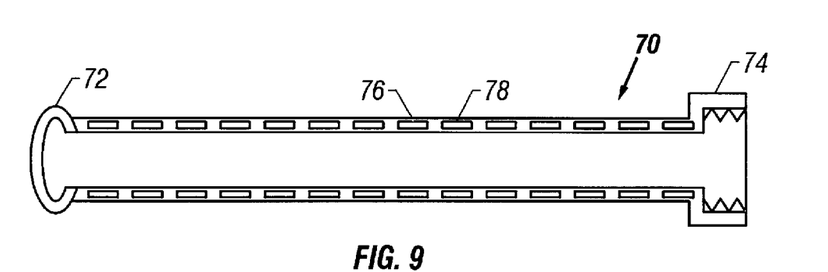
FIG. 9 is a sectional view of the tube of FIG. 8 taken along section lines XI—XI.

FIG. 9 shows the reinforcing coil 78 embedded within the wall 76 of tubing 70. Coil 78 is preferably a flat wire spring, preferably comprising stainless steel, but may also be formed of polymers (aramid fibers, KEVLAR fibers, etc.) or other biocompatible materials having the acceptable "non-stretch" characteristics described above. Also, the reinforcement may be formed as a round wire coil or as a braid (preferably flat ribbon, but round wire is also possible) of the materials described.

The tubing 70 enables both the applicator 50, and thus the user's hand to be distanced from the radiographic field or other viewing field, which is advantageous both for safety purposes as well as improving the procedure. This embodiment is particularly advantageous for the most frequent set-ups where bi-planar viewing is performed and two imaging devices are oriented at 90° to one another about the implantation site. One of the advantages which is gained that improves the procedure, is that the viewing instrumentation can be moved closer to the actual implantation site, thereby providing a more magnified view.

It is preferred that the tubing 70 is mounted to the pressure applicator prior to mounting on the cannula fitting 18. After the tubing 70 is mounted to fitting 52, the pressure applicator is filled with implant material as described above. A small amount of pressure is next applied to the implant material to express the implant material until a minimal amount exits the open end of the tubing (i.e., the end where connector 74 is located). The tubing 70 is then connected to the connector 18 of the cannula 10 for implantation of the implant material into the desired location. Although the foregoing is the desired order of connection so that the air space in the tubing can be prefilled with implant material, it is not the only possible progression for the procedure. Alternatively, the tubing 70 can be connected to the fitting 18 of the cannula 10 and the tubing 70 and cannula 10 are then backfilled with saline, implant material, or other biocompatible fluid to displace any air residing in the structures. After filling of the pressure applicator 50 with implant material, the tubing can be connected to the fitting 52 and implantation of the implant material can be rapidly commenced thereafter.

The present invention is not limited to use for percutaneous vertebroplasty, and the method described is only for purposes of illustration of a preferred use of the present invention. The substantially non-compliant conduit of the present invention can be used for any high pressure delivery of implant materials, and is especially valuable in those situations where the implant materials are particularly viscous. Other particularly advantageous uses are those where the implant material may or may not be particularly viscous, but where the delivery device adds a substantial amount of resistance to the delivery system, as in the cases where the material is delivered through a cannula, needle, or other relatively small bore, high resistance device.

EXAMPLES

Comparative Example

A polyurethane tubing with a reinforcing braid within its wall was measured to have an inside diameter of 0.072" and an outside diameter of 0.143" with a length of 12". Measurements of the outside diameter of the tubing were taken at the center of the length of the tube in increments of 200 psi, from 0 psi (atmospheric pressure) up to 1200 psi. This procedure was repeated for two more tubings having the same characteristics. Averaging the results from the three tubings, the compliance of this type of tubing at 1200 psi was calculated to be nearly 50%.

Example 1

A tubing comprising a wall formed of FEP with a stainless steel coil embedded in the wall was measured to have an inside diameter of 0.107" and an outside diameter of 0.182" with a length of 12". The stainless steel coil was formed of a wire having a 0.005" diameter. Measurements of the outside diameter of the tubing were taken at the center of the length of the tube in increments of 200 psi, from 0 psi (atmospheric pressure) up to 1200 psi. This procedure was repeated for two more tubings having the same characteristics. Averaging the results from the three tubings, the compliance of this type of tubing at 1200 psi was calculated to be about 8–10%.

Example 2

A tubing comprising a wall formed of PEEK with no reinforcing coil or braid was measured to have an inside diameter of 0.080" and an outside diameter of 0.125" with a length of 12". Measurements of the outside diameter of the tubing were taken at the center of the length of the tube in increments of 200 psi, from 0 psi (atmospheric pressure) up to 1200 psi. This procedure was repeated for two more tubings having the same characteristics. Averaging the results from the three tubings, the compliance of this type of tubing at 1200 psi was calculated to be about 1–2%.

Although there have been described devices for percutaneous delivery of a hard tissue implant material, with a limited selected number of alternative embodiments in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as set forth in the claims which follow.

What is claimed is:

1. A method of delivering implant material, comprising:
    inserting a substantially non-compliant delivery device into a tissue site where implantation of an implant material is desired;
    connecting an end of a flexible, substantially non-compliant, high pressure conduit to an input port of the delivery device;
    connecting an opposite end of said conduit to a high pressure applicator containing a predetermined volume of tissue implant material; and
    applying a high pressure to the implant material with said high pressure applicator, to drive the implant material through said conduit and said device and into the site.

2. The method of claim 1, wherein said applying a high pressure comprises applying a pressure of at least about 1000 psi.

3. The method of claim 2, wherein said applying a high pressure comprises applying a pressure of about 1000 to 2000 psi.

4. The method of claim 2, wherein said applying a high pressure comprises applying a pressure of up to about 3000 psi.

5. The method of claim 1, wherein a combined inside volume of said delivery device, conduit and high pressure applicator increases by less than about 25% during said applying a high pressure.

6. The method of claim 5, wherein said combined inside volume increases by less than about 20% during said applying a high pressure.

7. The method of claim 6, wherein said combined inside volume increases by less than about 10% during said applying a high pressure.

8. The method of claim 7, wherein said combined inside volume increases by less than about 5% during said applying a high pressure.

9. The method of claim 1, wherein said inserting a substantially non-compliant delivery device comprises placing a substantially non-compliant cannula into a hard tissue implant site.

10. The method of claim 1, wherein said delivery device comprises a substantially non-compliant cannula, and said inserting a substantially non-compliant device further comprises:
    inserting a stylet into the site where implantation of the implant material is desired; and
    guiding said cannula over said stylet into the site where implantation of a hard tissue implant material is desired.

11. The method of claim 10, further comprising:
    removing said stylet from within said cannula prior to said connecting an end of said substantially non-compliant, high pressure conduit to said cannula.

12. The method of any of claims 1 wherein the implant site is a vertebral implant site.

* * * * *